US012631619B2

(12) United States Patent
Gonzalez et al.

(10) Patent No.: US 12,631,619 B2
(45) **Date of Patent: *May 19, 2026**

(54) USE OF BIOLOGICAL SAMPLE REPRESENTATIVE OF A PASSENGER CABIN ON AN AIRCRAFT TO IDENTIFY ALL KNOWN MICROORGANISMS AND NON-DESCRIBED EMERGING PATHOGENS

(71) Applicant: B/E AEROSPACE, INC., Winston Salem, NC (US)

(72) Inventors: Arnau Castillo Gonzalez, Maarssen (NL); Antonio Martinez Murcia, Elche (ES)

(73) Assignee: B/E AEROSPACE, INC., Winston Salem, NC (US)

( * ) Notice: Subject to any disclaimer, the term of this patent is extended or adjusted under 35 U.S.C. 154(b) by 1205 days.

This patent is subject to a terminal disclaimer.

(21) Appl. No.: 17/518,348

(22) Filed: Nov. 3, 2021

(65) Prior Publication Data

US 2022/0155186 A1 May 19, 2022

Related U.S. Application Data

(60) Provisional application No. 63/114,330, filed on Nov. 16, 2020, provisional application No. 63/114,400, (Continued)

(51) Int. Cl.
*C12Q 1/686* (2018.01)
*B01L 1/00* (2006.01)
(Continued)

(52) U.S. Cl.
CPC .............. *G01N 33/497* (2013.01); *B01L 1/00* (2013.01); *B01L 3/021* (2013.01); *B01L 3/505* (2013.01);
(Continued)

(58) Field of Classification Search
CPC . C12Q 1/04; B64D 2013/0603; G01N 1/2226
See application file for complete search history.

(56) References Cited

U.S. PATENT DOCUMENTS

2003/0153021 A1* 8/2003 Lu .......................... C12M 41/36
435/287.1
2008/0003649 A1 1/2008 Maltezos et al.
(Continued)

FOREIGN PATENT DOCUMENTS

WO WO-03082425 A2 * 10/2003 ........... G01N 1/2273

OTHER PUBLICATIONS

Korves et al., "Bacterial communities in commercial aircraft high-efficiency particulate air (HEPA) filters assessed by PhyloChip analysis," Indoor Air, vol. 23, pp. 50-61. (Year: 2013).*
(Continued)

*Primary Examiner* — Young J Kim
(74) *Attorney, Agent, or Firm* — SNELL & WILMER L.L.P.

(57) ABSTRACT

A method for collecting and testing particulates from aircraft air is disclosed. The method includes capturing particulates in at least one of an outlet flow path or a recirculation flow path with a collector over a period of time, removing the collector from at least one of the outlet flow path or the recirculation flow path for testing, concentrating the collected sample, conducting a test on at least one particulate captured in the collector, relaying a result of the test to a central data center to store the results, and identifying a previously non-described emerging pathogens within the results.

15 Claims, 2 Drawing Sheets

Related U.S. Application Data filed on Nov. 16, 2020, provisional application No. 63/114,350, filed on Nov. 16, 2020, provisional application No. 63/114,157, filed on Nov. 16, 2020, provisional application No. 63/114,366, filed on Nov. 16, 2020, provisional application No. 63/114,064, filed on Nov. 16, 2020, provisional application No. 63/114,386, filed on Nov. 16, 2020, provisional application No. 63/114,339, filed on Nov. 16, 2020.

(51) Int. Cl.

| | |
|---|---|
| *B01L 3/00* | (2006.01) |
| *B01L 3/02* | (2006.01) |
| *B01L 7/00* | (2006.01) |
| *B64D 13/08* | (2006.01) |
| *C12Q 1/04* | (2006.01) |
| *C12Q 1/70* | (2006.01) |
| *G01N 1/10* | (2006.01) |
| *G01N 1/22* | (2006.01) |
| *G01N 1/40* | (2006.01) |
| *G01N 33/497* | (2006.01) |
| *G16B 10/00* | (2019.01) |
| *G16B 40/00* | (2019.01) |
| *G16B 50/10* | (2019.01) |
| *B64D 13/06* | (2006.01) |
| *H04L 67/12* | (2022.01) |

(52) U.S. Cl.

CPC ............... *B01L 7/52* (2013.01); *B64D 13/08* (2013.01); *C12Q 1/04* (2013.01); *C12Q 1/686* (2013.01); *C12Q 1/70* (2013.01); *G01N 1/10* (2013.01); *G01N 1/2226* (2013.01); *G01N 1/2247* (2013.01); *G01N 1/40* (2013.01); *G16B 10/00* (2019.02); *G16B 40/00* (2019.02); *G16B 50/10* (2019.02); *B01L 2200/028* (2013.01); *B01L 2200/10* (2013.01); *B01L 2200/18* (2013.01); *B01L 2300/023* (2013.01); *B01L 2300/18* (2013.01); *B64D 13/06* (2013.01); *B64D 2013/0603* (2013.01); *G01N 2001/1031* (2013.01); *G01N 1/2205* (2013.01); *G01N 2001/2244* (2013.01); *G01N 33/4975* (2024.05); *H04L 67/12* (2013.01)

(56) References Cited

U.S. PATENT DOCUMENTS

| | | | |
|---|---|---|---|
| 2008/0245706 | A1 | 10/2008 | O'Brien et al. |
| 2009/0035770 | A1 | 2/2009 | Mathies et al. |
| 2011/0159596 | A1 | 6/2011 | Keinan et al. |
| 2012/0122075 | A1 | 5/2012 | Call et al. |
| 2016/0025603 | A1 | 1/2016 | Kindt et al. |
| 2017/0009290 | A1 | 1/2017 | Ahmad et al. |
| 2019/0046985 | A1 | 2/2019 | Kang et al. |
| 2022/0057303 | A1* | 2/2022 | Surawski ............. G01N 1/2247 |
| 2022/0057304 | A1* | 2/2022 | Gonzalez ............... B64D 13/00 |
| 2022/0155187 | A1* | 5/2022 | Gonzalez ............. G01N 1/2247 |
| 2022/0155188 | A1* | 5/2022 | Gonzalez .................. B01L 7/52 |
| 2022/0155189 | A1* | 5/2022 | Gonzalez ............. G01N 1/2247 |
| 2022/0155191 | A1* | 5/2022 | Gonzalez ............... G16B 50/10 |

OTHER PUBLICATIONS

Sung et al., "Highly efficient in-line wet cyclone air sampler for airborne virus detection," Journal of Mechanical Science and Technology, vol. 31, No. 9, pp. 4363-4369. (Year: 2017).*

Extended European Search Report for European Patent Application No. EP21208622.7, dated Apr. 14, 2022.

Korves T.M., et al., "Bacterial communities in commercial aircraft high-efficiency particulate air (HEPA) filters assessed by PhyloChip analysis"; Indoor Air, vol. 23, No. 1, Jun. 8, 2012 (Jun. 8, 2012), pp. 50-61, XP055907740, DK; ISSN: 0905-6947, DOI: 10.1111/j.1600-0668.2012.00787.x; sections "Practical Implications"; "Materials and methods", "Aircraft and outdoor air samples"; first and second paragraph; "PCR amplification of 16S rRNA genes" .

Extended European Search Report dated Apr. 13, 2022, issued during the prosecution of European Patent Application No. EP 21208613.6.

Korves T. M., et al., "Bacterial Communities in Commercial Aircraft High-Efficiency Particulate Air (HEPA) Filters Assessed by PhyloChip Analysis", Indoor Air, vol. 23, No. 1, Jun. 8, 2012, pp. 50-61.

European Patent Office, European Office Action dated Jan. 25, 2024 in Application No. 21208613.6.

* cited by examiner

USE OF BIOLOGICAL SAMPLE REPRESENTATIVE OF A PASSENGER CABIN ON AN AIRCRAFT TO IDENTIFY ALL KNOWN MICROORGANISMS AND NON-DESCRIBED EMERGING PATHOGENS

CROSS-REFERENCE TO RELATED APPLICATION

This Application claims the benefit of U.S. Provisional Application 63/114,330 filed on Nov. 16, 2020. This Application claims the benefit of U.S. Provisional Application 63/114,339 filed on Nov. 16, 2020. This Application claims the benefit of U.S. Provisional Application 63/114,350 filed on Nov. 16, 2020. This Application claims the benefit of U.S. Provisional Application 63/114,064 filed on Nov. 16, 2020. This Application claims the benefit of U.S. Provisional Application 63/114,366 filed on Nov. 16, 2020. This Application claims the benefit of U.S. Provisional Application 63/114,157 filed on Nov. 16, 2020. This Application claims the benefit of U.S. Provisional Application 63/114,386 filed on Nov. 16, 2020. This Application claims the benefit of U.S. Provisional Application 63/114,400 filed on Nov. 16, 2020. The entire contents of these applications are incorporated herein by reference in their entirety.

BACKGROUND OF THE INVENTION

1. Field of the Invention

The present application is related to a system and method used collect a representative air sample of an aircraft, more specifically to a method and systems for collecting and analyzing an air sample on an aircraft to determine all genetic sequences present in the sample and identifying the microbiota, including non-described emerging pathogens.

2. Description of Related Art

The spread progression of SARS-CoV-2 around the world has risen a red flag: Economic economic globalization creates systemic risks. As trade, finance, travel, cyber and other networks grow in scale and interact, they become more complex and unstable. The transporters of the goods of the global economy, such as major airport hubs, are also spreaders of the pathogens. The 2008 global financial crisis provided a dramatic example of how contagions could spread from the US to global markets overnight. So too has the rapid spread of cyber viruses. In health, rising life expectancy and success in preventing a repeat of the devastating influenza pandemic of 1918, which infected about one-third of the world's population and killed as many as 50 m people, has created a false sense of security. But the world is now more interdependent. For example, China represents almost one-fifth of global output, is integral to global supply chains, and its tourists spend over $260 billion annually. The CovidCOVID-19CoVID-19 pandemic shed light on the need for better monitoring, detecting, and isolating ill passengers, specifically due to the havoc that was wreaked detrimental impact on the global economy, specifically air travel due to closed borders, movement restrictions, and testing requirements.

However, the COVIDCoVID-19 pandemic the air travel industry has proven that air travel can be safe and that aircraft cabins have a well-managed airflow that inhibits minimize the risk for transmission of virus, and that being seated onboard an aircraft is safer than shopping in large stores. Governments and other authorities need to assume that aircraft are contaminated until proven "clean", as 25% of COVID-19 cases are asymptomatic or pre-symptomatic; but still contagious. Thus, if borders shutdown and a drastic reduction in international travel global passenger travel is greatly reduced. To date travelers and governments have relied on individual diagnostic tests. The uncertainty of the results has reduced people's inclination to travel and subsequent airline inclination to maintain routes.

Accordingly, there is still a need in the art for unknown virus and pathogen identification and detection systems and methods to be implemented in the cabins of commercial aircrafts. The present disclosure provides a solution for this need.

SUMMARY OF THE INVENTION

A method for collecting particulates from aircraft air is disclosed. The method includes capturing particulates in at least one of an outlet flow path or a recirculation flow path with a collector for a period of time, removing the collector from at least one of the outlet flow path or the recirculation flow path for testing, inserting a clean collector into at least one of the outlet flow path or the recirculation flow path for use during another period of time, conducting a test on at least one particulate captured in the collector, relaying a result of the test to a central data center to store the results, and identifying a previously non-described emerging pathogens within the results. The test can include a pathogen detector or a chemical or irritant detector. Or a genetic sequence determination (a sequencer)

The method can further include aggregating a plurality of tests to develop a pattern of all microorganisms (bacteria, virus, fungi) including the pathogens. The method can include receiving an alarm or signal to aggregate a particular type of result. The test can include phylogenetic analysis and sequence comparison (sequence alignments) with databases containing all previously described microorganisms. The method will include the identification of sequences belonging to known pathogen and these corresponding to non-described taxa. The method will include a search for possible pathogenic characteristics of non-described taxa which may emerge. The method can include communicating test results to corresponding health authorities or communicating test results aggregates to corresponding health authorities.

A system for monitoring aircraft air is also disclosed. The system can include a collector for collecting particulate samples positioned within at least one of an outlet flow path or a recirculation flow path, at least one of an outflow valve positioned in the outlet flow path downstream from the collector or a HEPA filter positioned in the recirculation flow path downstream from the collector, a storage unit or database for storing collected samples or analyzed sample materials of known species and previously non-described emerging pathogens within the results. The system can include the collector includes a filter material, or a buffer-cyclonic collector. The storage unit can be at a remote location with respect to the aircraft.

The samples can include particles and droplets exhaled from passengers throughout a duration of a flight. The collector can include an adaptor and a filter material operatively connected to the adaptor, cyclonic collection in a buffer, etc. The database can include DNA and RNA sequences of all described microbial species, including DNA and RNA sequences different to all these with a known pathogen.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
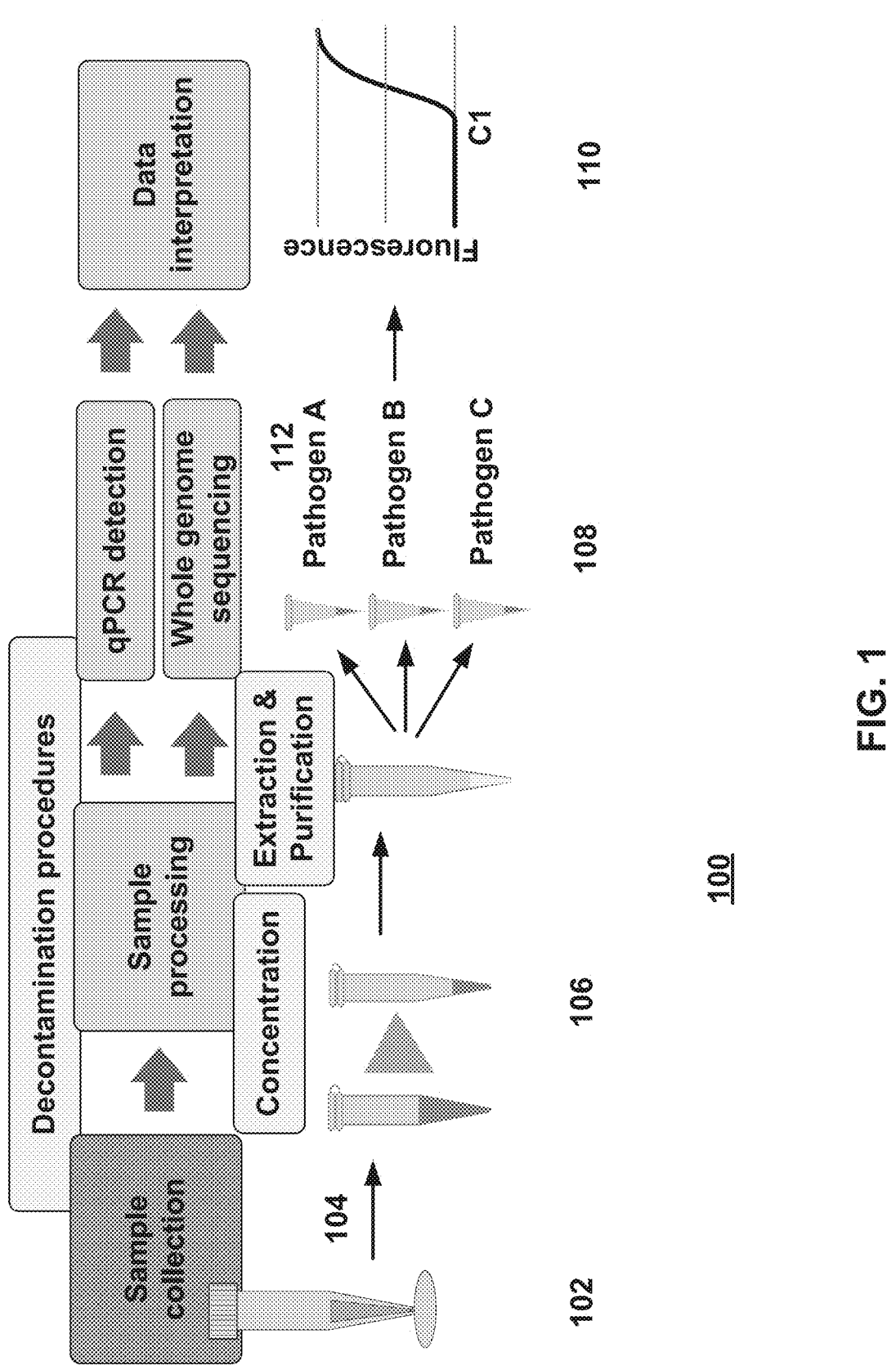
FIG. 1 is a schematic view of a method for collecting and analyzing an aircraft air sample.
Figure 2:
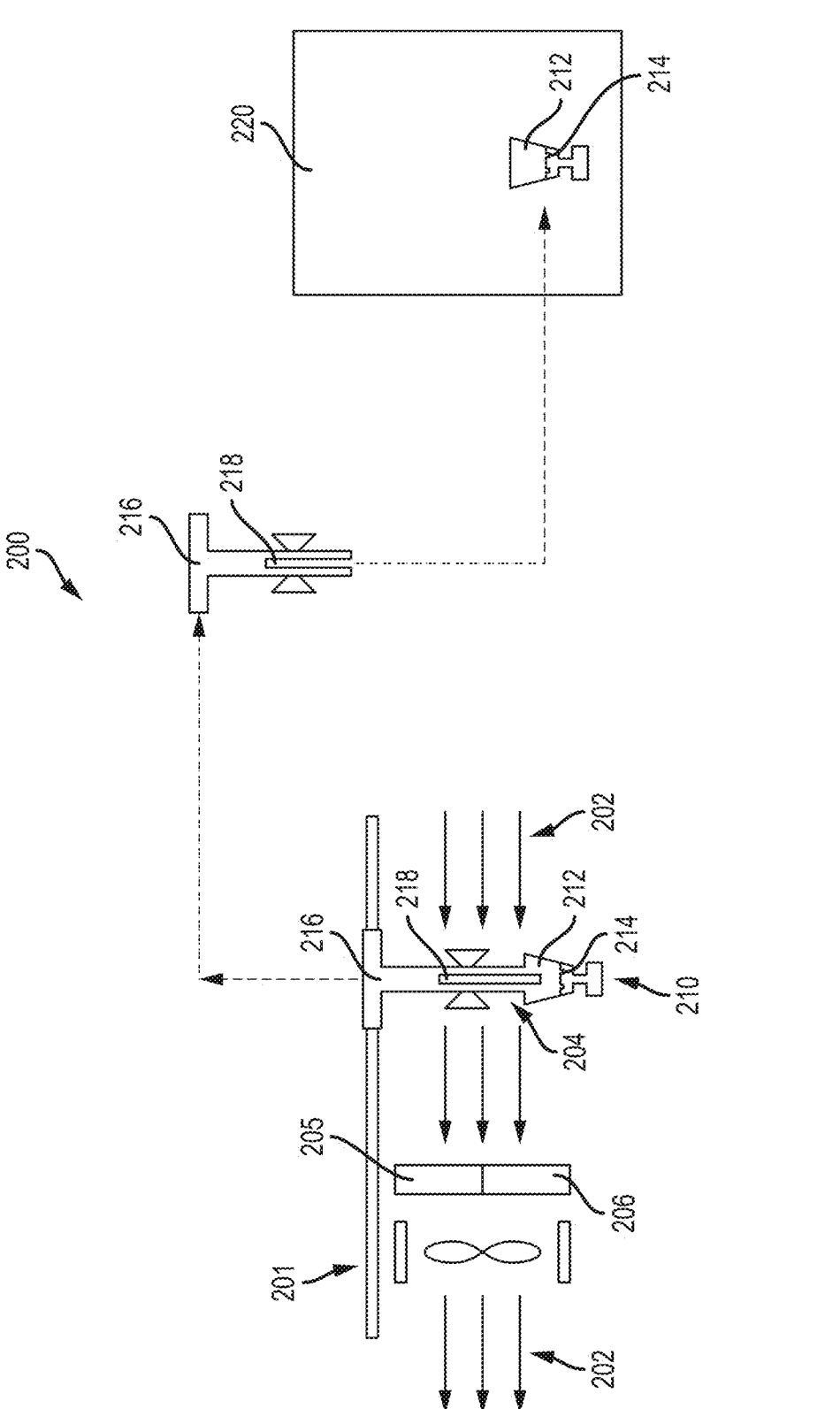
FIG. 2 illustrates a system for collecting and analyzing an aircraft air sample.

Reference will now be made to the drawings wherein like reference numerals identify similar structural features or aspects of the subject disclosure. For purposes of explanation and illustration, and not limitation, a schematic view of an exemplary embodiment of a method monitoring aircraft air in accordance with the disclosure showing a collector within a cabin of an aircraft is shown in FIG. 1 and is designated generally by reference character 100. The systems and methods described herein can be used to provide multiple options for monitoring aircraft air. The embodiments of the system for monitoring aircraft air of the present disclosure provide a means for testing air in any enclosed space such as inside an aircraft, and allows for the identification and detection of a virus or other contaminant, such as a previously undescribed contaminant.

As shown in FIG. 1, a method 100 for collecting and testing particulates from aircraft air is disclosed. The method 100 includes capturing 102 particulates in at least one of an outlet flow path or a recirculation flow path with a collector over a period of time, removing the collector 104 from at least one of the outlet flow path or the recirculation flow path for testing, concentrating the collected sample 106, conducting a test 108 on at least one particulate captured in the collector, relaying a result 110 of the test to a central data center to store the results, and identifying 112 a previously non-described emerging pathogens within the results. The test can includes a pathogen detector, such as a Pathogen/contaminant diagnostic tester, such as a polymerase chain reaction (PCR) test, something biological that includes RNA or DNA, or a chemical or irritant that is produced by machinery.

The method 100 also requires include aggregating a plurality of tests from various flight around the world or from a particular destination to develop a pattern of pathogens or irritants. The method can also include receiving an alarm or signal from a central health authority, from a flight operator, or an airport to aggregate a particular type of result and provide a pattern, to predict whether a new strain of a disease is emerging. The test can include doing phylogenetic analysis on the collected samples.

The method 100 can include communicating the individual test results to corresponding health authorities of a particular country or region or communicating test results aggregates to corresponding health authorities. This communication can be requested by the authorities themselves when cases at a local hospital exceed some threshold. The tests can also be collected and stored without testing, and can then be tested when a specific pattern or pathogen needs to be linked to a disease that is spreading across a particular region. It is also considered that the collected samples can be tested for a new DNA and/or RNA strain that has not been linked to a disease previously.

A system 200 for monitoring aircraft air and doing the tests described above is also disclosed. The system 200 includes a collector 210 for collecting samples containing particles from the air. For example, the collector 210 may be positioned within an airflow path 202 of an aircraft. Airflow path 202 may be at least one of an outlet flow path or a recirculation flow path. System 200 may comprise an outflow valve 205 positioned in the outlet flow path downstream from the collector 210. System 200 may comprise a HEPA filter 206 positioned in the recirculation flow path downstream from the collector 210. System 200 may comprise a storage unit or database for storing collected samples. System 200 may comprise a tester for testing and analyzing sample materials. Sample materials may comprise previously non-described emerging pathogens. The storage unit and database may be configured to retain samples and data related to the samples. The storage unit and database may be configured to retain samples and data related to the previously non-described emerging pathogens. The collectors 210 can be analyzed in various ways, including removing a portion of the collector, scrubbing the collectors to remove the bio sample, or using a buffer containing reagents to capture the sample. Once the samples are collected the samples can be stored within a storage (−20° C.) unit indefinitely until they are required to be tested. The storage unit can be at a remote location with respect to the aircraft, alternatively, the samples can be analyzed, by PCR and sequencing, with the results being stored at a remote database for pattern analysis at a later date.

In various embodiments, the collector 210 may comprise a test vial 212. Test vial 212 may contain a reagent 214. In this manner, the collector 210 may be configured to concentrate a collected sample (i.e. particulate samples) in a format or a size usable for genetic PCR testing. In this manner, samples may be tested during flight, upon landing and prior to disembarking passengers, or prior to allowing passengers into common areas. In various embodiments, the collector 210 may comprise an adapter 216. Adapter 216 may be configured to be accessible from within the aircraft cabin. For example, adapter 216 may be accessible from a cabin floor 201. Adapter 216 may be configured to extend at least partially into the airflow path 202. The test vial 212 may be removable from adapter 216. In this manner, test vial 212 may be disconnected from adapter 216 for analysis within a test machine 220. In various embodiments, the collector 210 may comprise a filter material 218. Filter material 218 may be configured to direct particulate samples captured from airflow 202. Filter material 218 may be configured to direct particulate samples captured from airflow 202 to the test vial. In this manner, particulate samples may be mixed with the reagent 214. In various embodiments, collector 210 may comprise a buffer-cyclonic current.

The samples can include particles and droplets exhaled from passengers throughout a duration of a flight. The collector can include an adaptor and a filter material operatively connected to the adaptor, buffer-ciclonic, etc. The database can include DNA and RNA sequences corresponding to all known taxa, and more specifically DNA and RNA sequences not corresponding to any of all known pathogens.

The methods and systems of the present disclosure, as described above and shown in the drawings, provide for air sample data collection system and method with superior properties. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A system for monitoring aircraft air comprising:
a collector for collecting particulate samples positioned within at least one of an outlet flow path or a recirculation flow path, the collector comprising:
a test vial and a reagent disposed within the test vial,
an adaptor configured to be accessible from within an aircraft cabin and configured to extend at least partially into the outflow path, and
a local filter material disposed within the adaptor, wherein the local filter material is configured to direct the particulate samples to the test vial for mixing with the reagent;
at least one of an outflow valve positioned in the outlet flow path downstream from the collector or a HEPA filter positioned in the recirculation flow path downstream from the collector; and
a storage unit or database for storing collected samples or analyzed sample materials of previously non-described emerging pathogens within the collected particulate samples.

2. The system of claim 1, the storage unit is at a remote location with respect to the aircraft.

3. The system of claim 1, wherein the collector is configured to concentrate the samples at a concentration suitable for a direct genetic PCR test-throughout a duration of a flight.

4. The system of claim 1, wherein the database includes DNA and RNA sequences.

5. The system of claim 1, wherein the database includes DNA and RNA sequences with previously unassigned disease identifiers.

6. The system of claim 1, wherein the collector includes a buffer-cyclonic current.

7. The system of claim 1, wherein the test vial is removable from the adaptor.

8. A method for collecting particulates from aircraft air comprising:
capturing particulates with an aircraft cabin air with a collector for a period of time, the collector comprising:
a test vial and a reagent disposed within the test vial,
an adaptor configured to be accessible from within an aircraft cabin and configured to extend at least partially into the outflow path, and
a local filter material disposed within the adaptor, wherein the local filter material is configured to direct the particulate samples to the test vial for mixing with the reagent;
removing the collector from for testing;
conducting a test on at least one particulate captured in the collector;
relaying a result of the test to a central data center to store the results; and
identifying all previously known pathogens and non-described emerging microorganisms within the results.

9. The method of claim 8, further comprising aggregating a plurality of tests to develop a pattern of genetic sequences.

10. The method of claim 8, further comprising receiving an alarm to aggregate a particular type of result.

11. The method of claim 8, wherein the test includes phylogenetic analysis, symptom comparison, or identification of new biological lineages.

12. The method of claim 8, further comprising communicating test results to corresponding health authorities.

13. The method of claim 8, further comprising communicating test results aggregates to corresponding health authorities.

14. The method of claim 8, wherein the test includes a pathogen/contaminant diagnostic device.

15. The method of claim 8, wherein the test includes a chemical or irritant detector.

* * * * *